US009526868B2

(12) United States Patent
Bennett

(10) Patent No.: US 9,526,868 B2
(45) Date of Patent: Dec. 27, 2016

(54) INTRAVENOUS CATHETER PROTECTIVE COVER

(76) Inventor: Tionne Allen Bennett, Anaheim, CA (US)

(*) Notice: Subject to any disclaimer, the term of this patent is extended or adjusted under 35 U.S.C. 154(b) by 1617 days.

(21) Appl. No.: 11/257,224

(22) Filed: Oct. 24, 2005

(65) Prior Publication Data

US 2007/0106222 A1    May 10, 2007

(51) Int. Cl.
*A61M 5/32* (2006.01)
*A61M 25/02* (2006.01)
*A61M 5/158* (2006.01)

(52) U.S. Cl.
CPC ............ *A61M 25/02* (2013.01); *A61M 5/158* (2013.01); *A61M 2025/0246* (2013.01); *A61M 2025/0266* (2013.01)

(58) Field of Classification Search
CPC .................... A61M 25/02; A61M 2025/0246; A61M 2025/028; A61M 3/027
USPC ......... 604/174, 175, 179, 180; 128/877, 888
See application file for complete search history.

(56) References Cited

U.S. PATENT DOCUMENTS

| 2,314,724 | A | * | 3/1943 | Marsan | 604/338 |
|---|---|---|---|---|---|
| 3,194,235 | A | * | 7/1965 | Cooke | 128/888 |
| 3,900,026 | A | * | 8/1975 | Wagner | 128/888 |
| 4,633,863 | A | * | 1/1987 | Filips et al. | 128/846 |
| 4,679,553 | A | * | 7/1987 | Proulx et al. | 128/846 |
| 5,074,847 | A | * | 12/1991 | Greenwell et al. | 604/174 |
| 5,238,010 | A | * | 8/1993 | Grabenkort et al. | 128/888 |
| 5,336,204 | A | * | 8/1994 | Matyas | 604/263 |
| 6,113,577 | A | * | 9/2000 | Hakky et al. | 604/174 |
| 6,428,515 | B1 | * | 8/2002 | Bierman et al. | 604/174 |
| 6,827,707 | B2 | * | 12/2004 | Wright et al. | 604/180 |
| 2002/0133121 | A1 | * | 9/2002 | Bierman | 604/174 |

* cited by examiner

*Primary Examiner* — Kevin C Sirmons
*Assistant Examiner* — William Carpenter
(74) *Attorney, Agent, or Firm* — Fish & Tsang LLP

(57) ABSTRACT

A protective cover or patch for covering and securing a catheter at the site of insertion of the needle into the patient's skin includes a single piece cover having a portion disposed about the perimeter of the patch bearing an adhesive coating and adapted for securement to a patients skin in the vicinity of the site of insertion, a bulbous chamber disposed inwardly of the perimeter portion, and a connecting portion disposed between the first portion and the chamber portion, the chamber portion defining a chamber for receiving one end of the catheter and extending substantially diametrically from one side of the perimeter to the other, and resilient tubing engagement elements positioned on opposite sides of the chamber. The chamber of the protective patch includes a roof portion raised above the plane defined by said perimeter of the patch.

14 Claims, 3 Drawing Sheets

INTRAVENOUS CATHETER PROTECTIVE COVER

BACKGROUND OF THE INVENTION

1. Field of the Invention

The present invention relates to intravenous catheters, and more particularly to devices for securing catheters to the location at which the catheter is attached to the patient. Even more particularly, the present invention relates to a single piece article functioning to cover and secure a catheter at a location where the catheter has been inserted into the patient's skin, and a method of using the article.

2. Description of the Related Art

Typically, when a vascular catheter is placed, for example for intravenous administration of fluids, a combined catheter and needle is used to create the vascular puncture after which the needle is removed and the hub of the remaining catheter attached to a source of infusion liquid. Generally, It is necessary to stabilize the catheter in relation to the blood vessel to prevent movement of the catheter to preclude catheter withdrawal, undesirable additional blood vessel punctures and the like. The catheter hub is typically stabilized by taping the hub and associated tube fittings to the patient's skin in the area adjacent the vessel puncture.

Using precautions, such as sterile gloves, while inserting the catheters has made the process of securing these catheters complicated. Indeed, in general, it is difficult to apply sticky tape to the skin while wearing gloves. In addition, the extra movement needed to reach for and to apply such tape risks the loss of the unsecured catheter. This is particularly true where the catheter has been placed in a child. As a result, it is not uncommon for the nurse or medical assistant to be forced to remove the gloves so that the catheter can be secured. Thus, the nurse or medical assistant is left without any protection for himself/herself while attempting to secure the catheter in its proper position.

There have been attempts in the past to address the foregoing problem of stabilization of an inserted needle or catheter immediately following vein puncture.

One approach has been to provide an adhesive surface on the underside of an element bearing wings provided on the catheter hub. Such intravenous needle assemblies are shown, for example, in U.S. Pat. No. 4,324,236 and U.S. Pat. No. 4,627,842. A difficulty encountered with such prior art products, however, is that the protective covering for the adhesive on the wings must be removed before the needle is inserted into the vein so that it may be thereafter adhered to the skin surface. Providing an adhesive surface that is exposed before vein puncture, however, risks premature adhesion to the skin and/or adhesion to the medial care provider's gloves.

Another approach has been to provide an anchoring system, including a device that permits a portion of a catheter or similar medical article to be anchored to a patient, preferably without the use of adhesive or needles. The anchoring system includes an anchor pad and a retainer mounted on the anchor pad. The retainer is attached to the anchor pad which includes adhesive for attaching the pad to the patient's skin at the puncture site. A medical article is secured within the channel by capturing and holding a radially extending element on the medical article. One of the notable features of this system is that correct positioning of the catheter relative to the anchoring member can be achieved. However, once the catheter is secured at the site of insertion, there is no cover or protective structure that will prevent the accidental dislodgement of the catheter from the patient's skin.

Also known and considered relevant are U.S. Pat. Nos. 6,673,046, 6,770,055, D492,411, 6,689,104, 6,663,600, 6,582,403, 6,572,588, 6,551,285, D470,936, 6,491,664, 6,447,485, 6,428,516, 6,428,515, 6,413,240, 6,361,523, 6,290,676, 6,283,945, 6,224,571, 6,213,979, 6,132,398, 6,117,163, D425,619, 5,947,931, 5,941,263, D404,815, 5,855,591, 5,833,667, 5,827,230, 5,800,402, 5,702,371, 5,693,032 and D377,831.

SUMMARY OF THE INVENTION

The catheter cover structure provided in accordance with the invention was designed to provide an easy way to secure a catheter to a patient's skin at or in the vicinity of a catheter puncture site, while maintaining hygienic precautions and avoiding premature adhesion to the skin surface. In the presently preferred embodiment, the catheter cover structure of the present invention is configured to be engaged with, and to secure a catheter at, a location in the near vicinity of the puncture site.

In one aspect of the invention, the cover comprises a shield having a central dome-shaped portion for receiving and protecting the portion of the catheter inserted into the patient as well as a portion of the catheter tubing extending away from the puncture site, and a perimeter defining a bearing surface for engaging the patient's skin and supporting the shield about the puncture site.

In another aspect of the invention, the cover further includes side portions disposed on adjacent opposing sides of the cavity of the central portion, the side portions each supporting on an outer surface retention means for holding a portion of the catheter tubing that extends from within the central cavity. Each side portion slopes from its skin engaging perimeter to the dome portion to permit objects hitting the cover to be deflected and the cover from being dislodged.

Yet another aspect of the invention is that the cover includes a first surface for adhesion to the patient's skin and a second opposing surface on which the retention means are mounted, wherein the central cavity of the cover is defined by an upstanding elongated portion extending across the lateral extent of the cover. In one version of the invention, the perimeter of the cover has a circular configuration. In another version of the invention, the perimeter of the cover has a multi-sided, somewhat diamond-shaped configuration.

In yet another aspect of the invention, the central portion of the cover further includes a chamber within which a cannula and needle is received and protected against accidental dislodgement. The chamber extends laterally or diametrically, depending on whether the cover has a substantially square shape or a substantially circular shape, respectively, from one side of the cover to the opposite side, and includes, at one end of the chamber wall, catheter engagement means extending across the chamber and having an opening therein sized to snugly receive the diameter of a catheter and a narrowed neck portion at a location remote from the upper side of the cover. The catheter tubing is secured within the cover by engaging the neck portion of the catheter engagement means about the catheter diameter. The neck portion of the cover, when the catheter tubing is held in the wall opening, forces a slight constriction of the catheter tubing (if the tubing is flexible or resilient enough to be capable of constriction) or engages the catheter tubing with a tight friction fit as the tubing passes the constriction.

In still another aspect of the invention, there is provided on the cover at regions remote from the chamber catheter resilient retainers to permit the slack in the end of the catheter extending outwardly from the chamber to be taken up by winding the protruding portion of the catheter around the perimeter of the cover and using the retainers to secure the protruding end against the cover.

Other objects, advantages and features of the invention will become more apparent, as will equivalent structures which are intended to be covered herein, with the teaching of the principles of the invention in connection with the disclosure of the preferred embodiments thereof in the specification, claims and drawings in which:

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a novel construction and method for securing a catheter at the site of insertion of the catheter needle into a patient.

Figure 1:
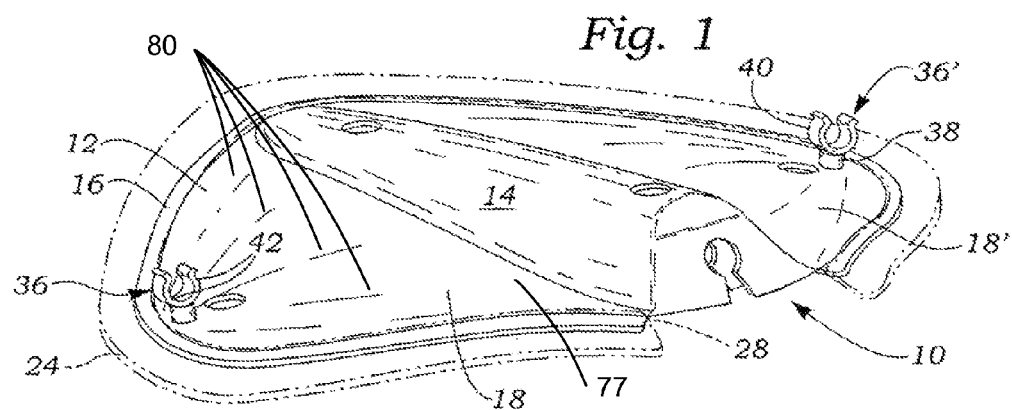
FIG. 1 is a top perspective view of the cover of the present invention.
Figure 2:
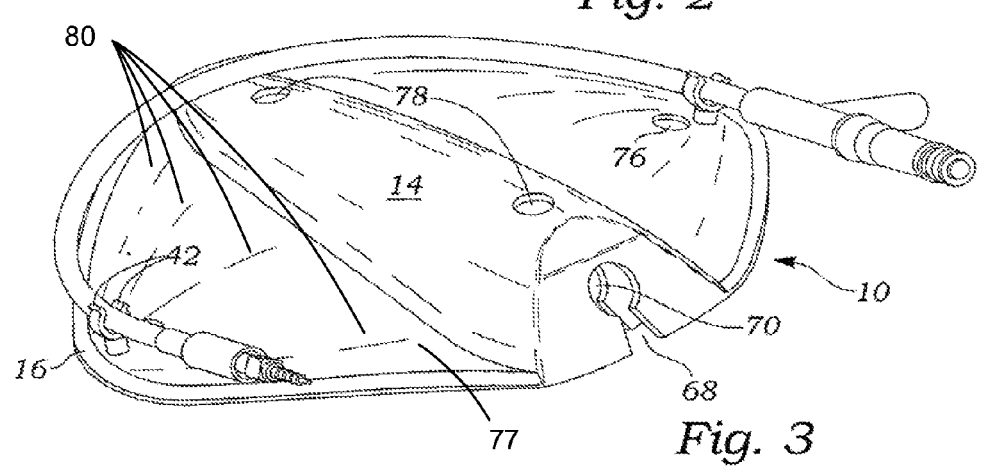
FIG. 2 shows a portion of a catheter secured to the cover shown in FIG. 1.
Figure 3:
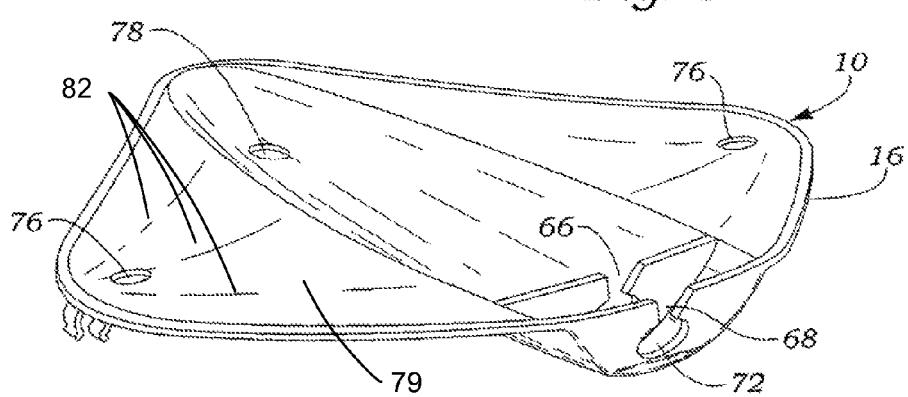
FIG. 3 is a view of the underside of the cover shown in FIG. 1.
Figure 4:
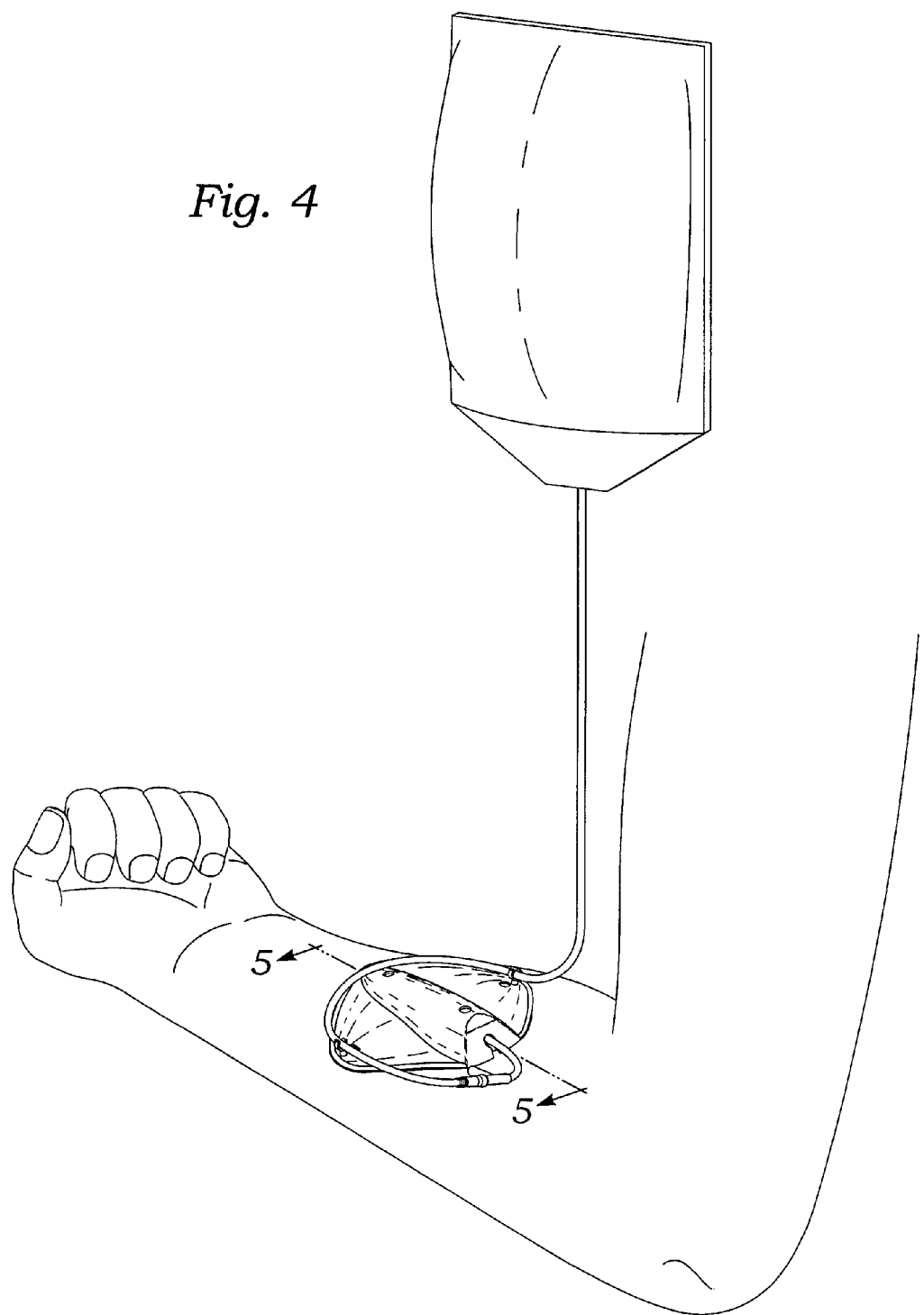
FIG. 4 illustrates the combined catheter and cover secured to a patient's arm.

Referring now to the various figures of the drawing, the shield or cover 10 of the present invention is made of non-flexible material and includes a body 12 having a central chamber 14, an edge portion 16 extending about the perimeter of the body, and side portions 18, 18' disposed on opposite sides of the chamber 14. As shown in FIGS. 1-3, the side portions 18, 18' each include curved upper 77 and lower surfaces 79, which are depicted by use of curved lines 80 and 82. The edge portion 16 is defined by a relatively narrow-width peripheral region arranged about the perimeter of the body, and preferably carries on its underside a layer of adhesive 26 (see FIG. 5). Alternatively, the edge portion 16 of the cover 10 could be secured to the patient's skin by disposing about the outer perimeter of the edge portion a second member 24 having an adhesive layer on the bottom surface of a first region 26 thereof. A second inwardly located region 28 of the second member 24 is raised and captures and retains the edge portion 16 of the cover 10.

For the sake of description, the cover 10 includes a "front" portion 54 and a "rear" portion 52 (see FIGS. 6 and 7), and further has an inner surface that is disposed adjacent to the patient's skin when the cover is secured thereto, and an outer surface that is exposed to the ambient. A first chamber 12 extends "longitudinally" across the cover from the front portion 32 to the rear portion 34, and "laterally" between the side portions 18, 18', each of the latter having slightly arcuate cross-sections. Located at lateral extremities of the side portions of the first chamber are catheter tubing retention means 36, 36, each of which preferably comprise a stem 38 extending upwardly from the upper surface of a respective one of the side portions, and on each stem of which is supported a U-shaped member 40 including two opposing arms and a connecting bight portion. More preferably, the two arms 42, 42 are resiliently biased toward one another so that the tubing of the catheter is firmly gripped between the arms when the catheter is disposed therebetween (see FIG. 2).

Figure 6:
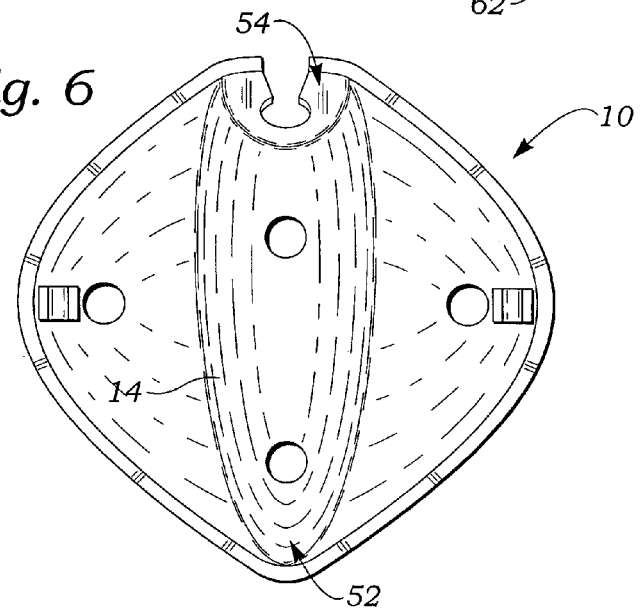
FIG. 6 is a top plan view of the cover of the present invention.
Figure 7:
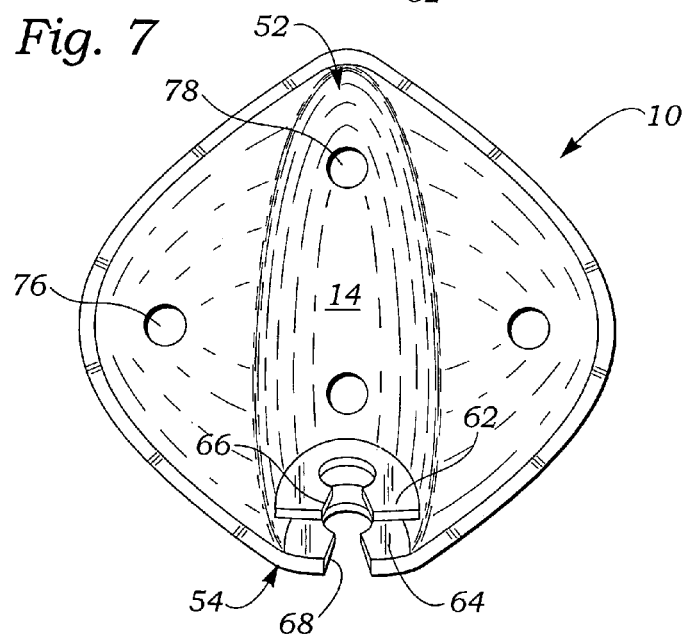
FIG. 7 is a bottom plan view of the cover of the invention.

Referring now to FIGS. 6, and 7, there is shown a second chamber 14 extending substantially longitudinally across the cover 10. The second chamber includes a blunted nose portion 52 at the rear portion of the cover 10 and a mouth portion 54 at the front portion of the cover 10. The mouth portion 54 has a lateral extent, that is a "side-to-side" extent, that is greater than the lateral extent of the nose portion 52. The second chamber 14 is defined by a U-shaped section of the cover that is raised above the upper surface of the first chamber of the cover 10. Preferably, the U-shaped section is disposed between the side portions 18, 18'. The U-shaped section of the second chamber 14 has a first height at the nose portion 52 that is nearly flush with the upper surface of the cover 10 and a second height at the mouth portion 54 that is substantially greater than the first height. Preferably, the height of the second chamber at the mouth portion is at least as great as the width of the second chamber at the mouth portion, and the length of the second chamber from front to back of the cover is at least twice as great as the height of the second chamber at the mouth portion thereof. More preferably, the length of the second chamber 14 from front to back of the cover is at least four times the height of the second chamber at the mouth portion thereof.

Figure 5:
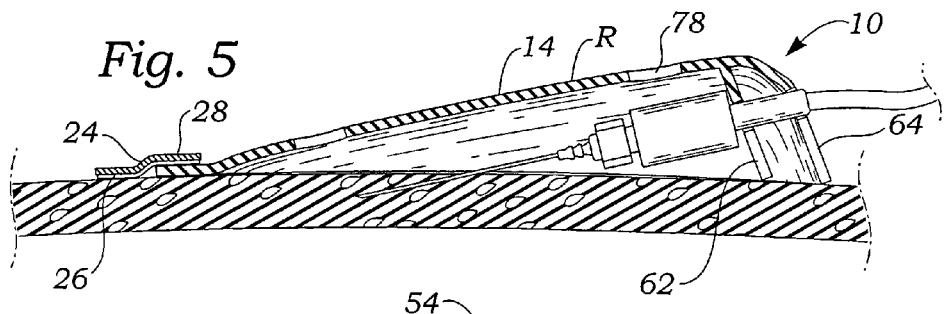
FIG. 5 is a cross-sectional view, taken along section line 5-5 in FIG. 4, of the cover of the invention secured to a patient's arm and also showing a catheter secured to the cover with the needle inserted in the patient's arm.

At the mouth portion of the second chamber 14 are inner and outer end walls 62, 64 (see FIGS. 3, 5 and 7). The end walls 62, 64 are arranged substantially perpendicular to the roof R of the chamber 14. Each of the inner and outer end walls are formed with slots 66, 68 that open toward the roof R of the second chamber, and a circular opening 70,72 at the inner end of each of the respective slots. The slots are defined by opposing wall surfaces that converge toward the openings 70, 72, respectively, and the openings in the parallel inner and outer end walls 62, 64 are concentric and disposed adjacent to the roof R of the second chamber 14.

Ventilation holes 76, 76 are provided in side portions 18, 18' of the first cover 12, and ventilation holes 78, 78 are provided at the top of the roof R of the second chamber 14. The side portions 18, 18' secure and stabilize the second chamber 14 atop the puncture site.

Those skilled in the art will appreciate that various adaptations and modifications of the invention as described above can be configured without departing from the scope and spirit of the invention. Therefore, it is to be understood that, within the scope of the appended claims, the invention may be practiced other than as specifically described herein.

What I claim is:

1. A protective cover for securing a catheter having a needle inserted at an insertion site in a patient's skin, comprising:

a single-piece element including (a) a first curved portion extending about the perimeter of the element and bearing an adhesive material configured to secure the element to a patient's skin about an insertion site, (b) a chamber portion disposed inwardly of the first portion, and (c) at least one raised wing having curved upper and lower surfaces extending from the skin-engaging first portion to the chamber portion;

wherein the at least one raised wing slopes upwardly with respect to the patient's skin from the skin-engaging first portion to the chamber portion, such that objects hitting the element are deflected;

wherein the chamber portion defines a protective housing for receiving one end of a catheter secured to a needle, the chamber portion extending substantially diametrically from one side of a perimeter to an opposing side; and a slot disposed within the chamber portion and carried by the element, wherein the slot is configured to prevent movement of the catheter with respect to the chamber portion.

2. The protective cover of claim 1, wherein the slot is carried by the chamber portion.

3. The protective cover of claim 2, wherein the slot is carried by the wings.

4. The protective cover of claim 1, further comprising a second slot disposed at one end of the chamber portion adjacent to the needle insertion site, and wherein the second slot is sized and dimensioned to resiliently engage at least one of the catheter and a catheter tubing.

5. The protective cover of claim 4, wherein the chamber portion further comprises:

a roof portion raised above a plane defined by the perimeter of the cover, and at least one side wall extending from the roof portion; and wherein the at least one side wall depends from the roof portion and is arranged perpendicular thereto;

and wherein the at least one side wall is divided into two separated portions which together cooperate to resiliently and frictionally engage and secure the catheter.

6. The protective cover of claim 1, wherein the chamber portion comprises a housing having a nose end and a mouth end, and wherein a width of the mouth end is greater than a width of the nose end, and wherein a height of the mouth end above the at least one wing is greater than a height of the nose end above the at least one wing.

7. The protective cover of claim 6, wherein the mouth end includes a catheter engaging section.

8. The protective cover of claim 7, wherein the chamber portion further comprises a roof portion, and the catheter engaging section comprises at least one wall depending from the roof portion, the at least one wall including a slot for receiving tubing associated with the catheter.

9. The protective cover of claim 1, further comprising first and second wings disposed on opposing sides of the chamber portion, and wherein the first and second wings are each configured to slope from a skin engaging perimeter to the chamber portion to (1) deflect objects hitting the cover and (b) prevent the cover from being dislodged from the patient's skin.

10. The protective cover of claim 1, further comprising an aperture configured to provide ventilation to an area between the skin and at least one of the chamber and the wing.

11. The protective cover of claim 10, wherein the aperture is disposed on the at least one wing.

12. The protective cover of claim 1, wherein the at least one wing comprises a fastener configured to secure a catheter tubing to the at least one wing.

13. The protective cover of claim 1, wherein the at least one wing comprises a curved upper surface that extends from the skin-engaging first portion to the chamber portion when the cover is disposed on the patient's skin.

14. A protective cover for securing a catheter having a needle inserted at an insertion site in a patient's skin, comprising:

a single-piece element including (a) a first curved portion extending about the perimeter of the element and bearing an adhesive material configured to secure the element to a patient's skin about an insertion site, (b) a chamber portion disposed inwardly of the first portion, and (c) at least one raised wing having curved upper and lower surfaces extending from the skin-engaging first portion to the chamber portion;

wherein the at least one raised wing slopes upwardly with respect to the skin-engaging first portion from the skin-engaging first portion to the chamber portion, such that objects hitting the element are deflected;

wherein the chamber portion defines a protective housing for receiving one end of a catheter secured to a needle, the chamber portion extending substantially diametrically from one side of a perimeter to an opposing side; and a slot disposed within the chamber portion and carried by the element, wherein the slot is configured to prevent movement of the catheter with respect to the chamber portion.

* * * * *